United States Patent [19]

Jenson

[11] Patent Number: 5,540,660
[45] Date of Patent: Jul. 30, 1996

[54] DISPOSABLE HYPODERMIC SYRINGE WITH NEEDLE SAFE FEATURE

[76] Inventor: Robert W. Jenson, 10 Oak Grove Way, Napa, Calif. 94558

[21] Appl. No.: 365,672

[22] Filed: Dec. 29, 1994

Related U.S. Application Data

[62] Division of Ser. No. 896,671, Jun. 10, 1992, Pat. No. 5,267,962, and a division of Ser. No. 161,938, Dec. 2, 1993, Pat. No. 5,380,285.

[51] Int. Cl.⁶ ..................................................... A61M 5/00
[52] U.S. Cl. ........................... 604/110; 604/195; 604/218
[58] Field of Search ..................................... 604/110, 187, 604/195, 263

[56] References Cited

U.S. PATENT DOCUMENTS

| | | | |
|---|---|---|---|
| 5,104,378 | 4/1992 | Haber et al. | 604/110 |
| 5,171,300 | 12/1992 | Blake, III et al. | 604/110 |
| 5,242,400 | 9/1993 | Blake, III et al. | 604/195 X |

*Primary Examiner*—John D. Yasko
*Attorney, Agent, or Firm*—Joseph L. Strabala

[57] ABSTRACT

In a syringe with a hollow cylindrical barrel with one closed end, a plunger having a length longer than the barrel mounted in the barrel for reciprocation, a handle on the distal end of the plunger extending from the barrel and a piston mounted on the opposite end of the plunger in the barrel and a hypodermic needle mounted in the closed end of the barrel being in communication with the interior of the barrel, the improvement of including a hollow tapered section in the barrel adjacent to its closed end, which tapered section in cooperation with the piston end of the plunger is operable to disable the syringe as the piston commences traversing this tapered portion of the barrel.

A desired embodiment has the tapered section or portion formed by a separate sleeve slidably mounted in the barrel with the hypodermic needle mounted in this sleeve with means to engage the sleeve whereby withdrawing the plunger from the barrel after its piston end has entered this tapered section will pull the sleeve and the attached needle into the barrel thereby preventing persons from thereafter being "pricked" by the sharp end of the "used" needle.

2 Claims, 5 Drawing Sheets

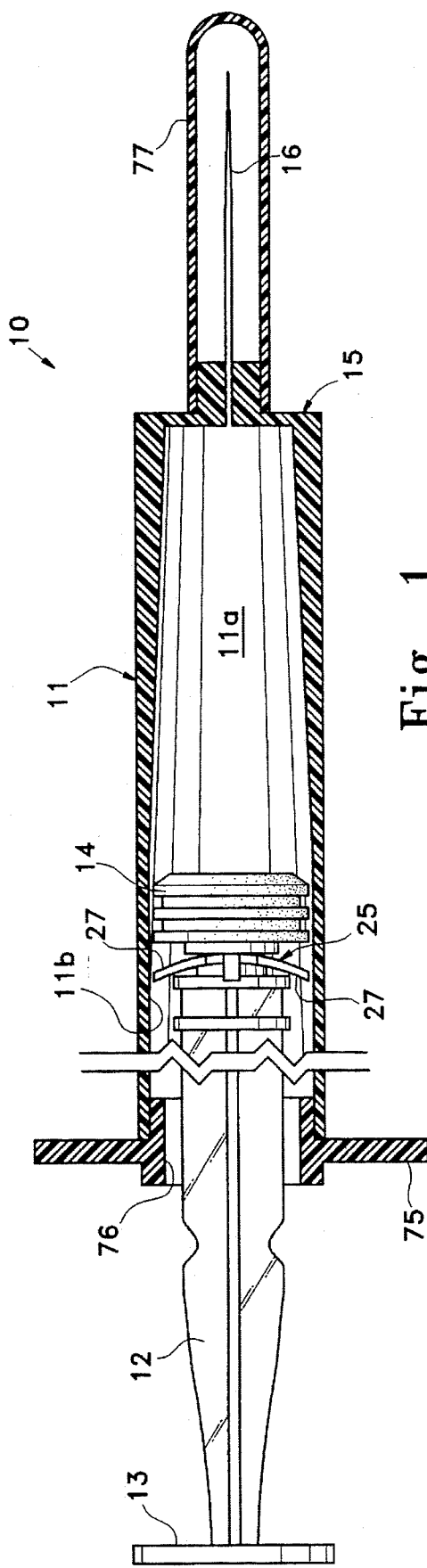
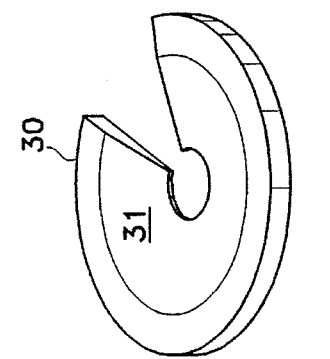
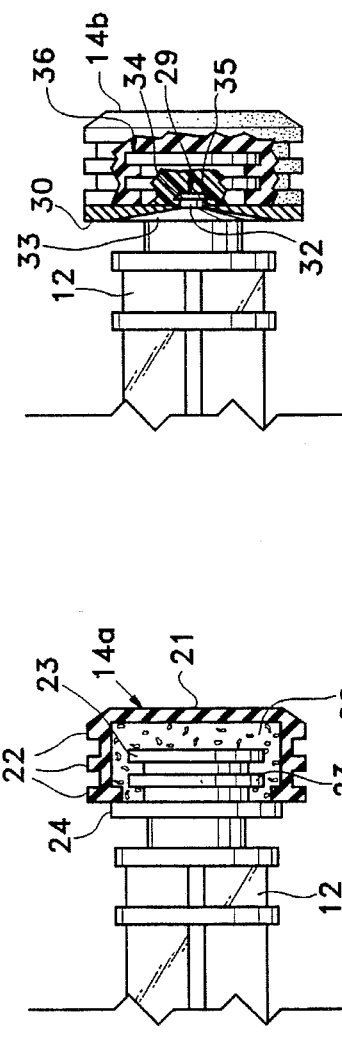
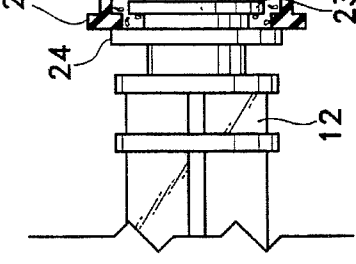
Fig. 1
Fig. 2
Fig. 3
Fig. 4

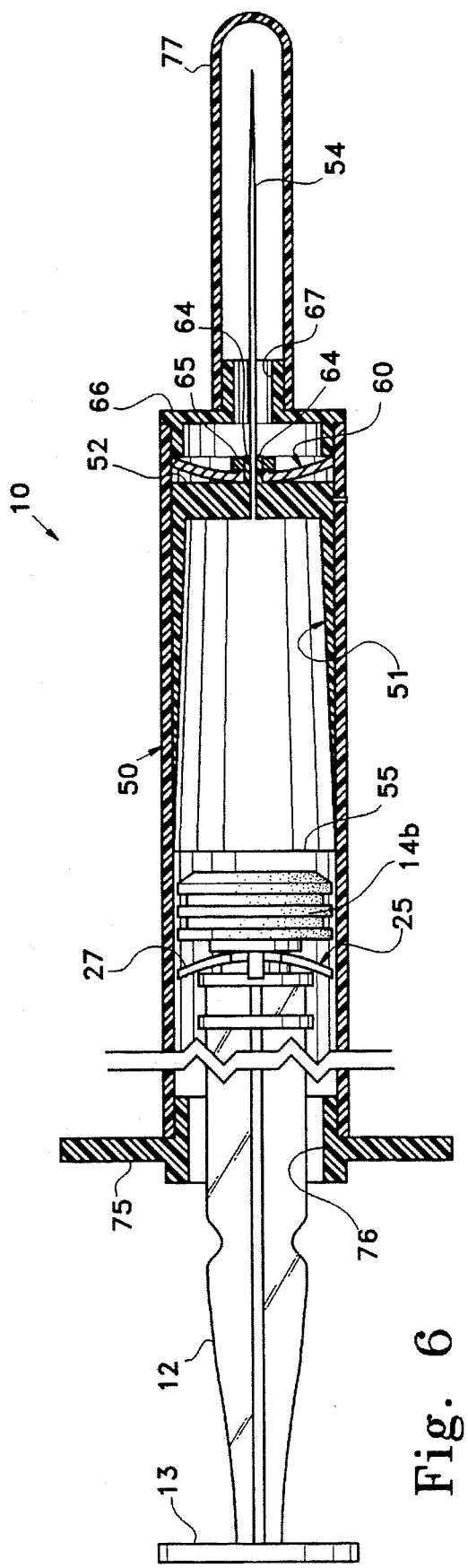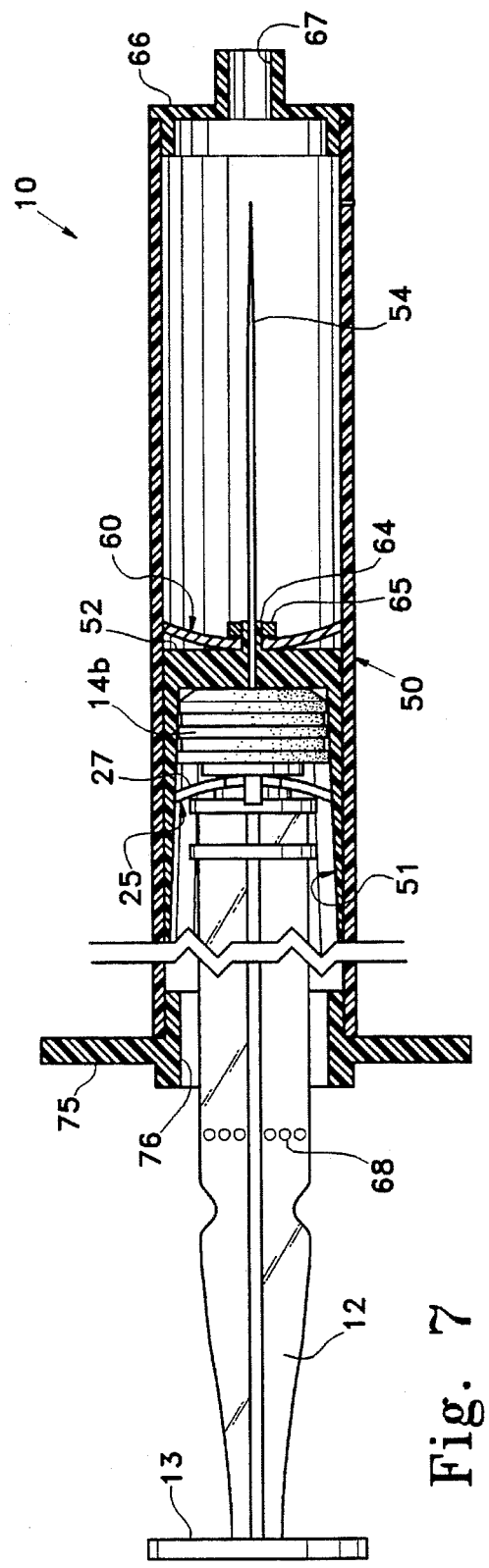
Fig. 6
Fig. 7

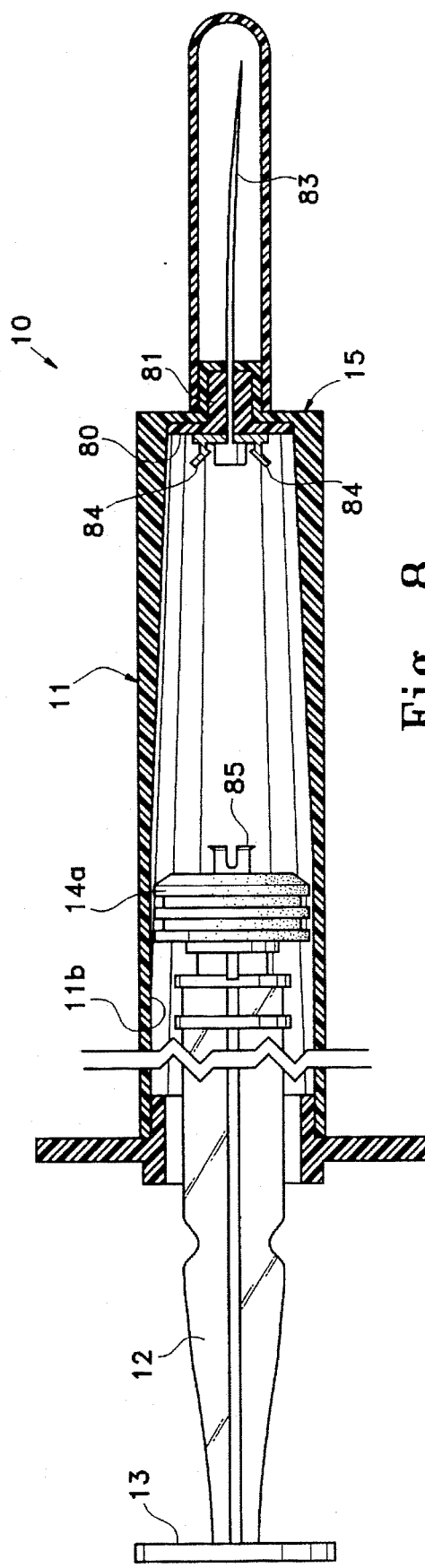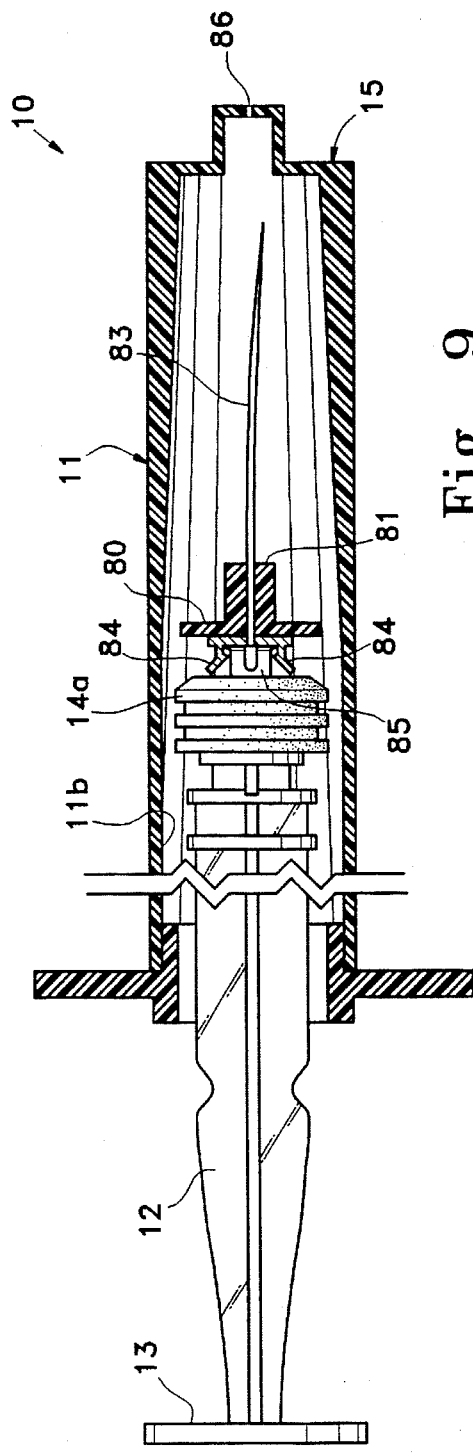

DISPOSABLE HYPODERMIC SYRINGE WITH NEEDLE SAFE FEATURE

This is a division of application Ser. No. 07/896,671 filed June 10, 1992, now U.S. Pat. No. 5,267,962 and divisional application Ser. No. 08/161,938 dated Dec. 2, 1993, now U.S. Pat. No. 5,380,285.

FIELD OF THE INVENTION

Hypodermic syringes today, in the interest of preventing the transmissions of disease, are often designed to be used only once by the medical community. As a result they must be constructed economically and provisions made for their disposal.

Unfortunately, there are those in our society, drug addicts, who use syringes for drugs, being neither trained in the prevention of diseases nor interested in sterile conditions achieved by single use, disposable syringes. Often drug addicts will use any functional syringe over and over again. Further such drug addicts, without any thought of the consequences, will share functioning syringes with their fellow drug addicts, creating a vehicle for transferring to one another a multitude of infections. An ominous infection which may be so transmitted is the HIV virus which causes auto immunodeficiency syndrome or AIDS. Contrary to popular opinion the HIV virus is often transmitted when an addict inject himself and then draws blood back into the syringe to flush the last microgram of the drug into his body. Within the syringe, and the hollow needle, the fragile HIV virus is protected, ready to be flushed into another addict's veins with the next dose of illegal drugs.

Recognition of these circumstances has lead to the development syringes which are termed "one shot" syringes; that is they are designed to be used only once. In the patent art, these "one shot" syringes abound. Examples are found in U.S. Pat. No. 4,7881,684 issued to Trenner, U.S. Pat. No. 4,863,427 issued to Cocchi; U.S. Pat. No. 4,887,999 issued to Alles; U.S. Pat. No. 4,874,372, issued to McArthur, et al.; U.S. Pat. No. 4,932,941, issued to Min, et al., U.S. Pat. No. 4,952,206 issued to Ibanez, et al. and U.S. Pat. No. 5,045,063 issued to Spielberg which were located in a search.

These patents disclose a number of approaches for disabling a hypodermic syringe to make it operable for only a single use. For example, one approach has been to employ recesses or apertures at the needle end of the syringe, whereby on completion of the injection "stroke", its piston will be locked in the needle end of the syringe; such devices are disclosed in U.S. Pat. Nos. 4,781,648 and 5,045,063. The deficiency of these types or syringes is that an addict simply does not complete the injection "stroke"; allowing him to use such a syringe over and over again.

U.S. Pat. No. 4,932,941 discloses a similar structure using tear drop projections in place of apertures or recesses to lock the piston in the needle end of the syringe when the injection "stroke" is completed; however it also suffers from the noted deficiency. In U.S. Pat. No. 4,887,999 a structure is shown in which projecting teeth are used and disposed in an axial alignment inside the syringe barrel forming a ratchet, making the plunger operable only in one direction. It overcomes one of the problems noted but is difficult to manufacture and use. These units also suffer from the fact that apertures and projections on the barrel's internal surface may cause undesirable bubbles in the medication in the syringe and/or loss of medication, as the piston travels over such irregularities on the inside barrel of the syringe.

Also suffering from the first mentioned problem is the device shown in U.S. Pat. No. 4,952,206 which drives a seal into the needle orifice, closing it off, when the injection "stroke" terminates its piston against it. Its disabling feature can also be circumvented by not fully completing tale injection "stroke". A related device is that shown in U.S. Pat. No. 4,863,427 which punctures the piston diaphragm or breaks off the piston from the plunger when the injection "stroke" is completed. By not fully completing an injection "stroke" its disabling feature can likewise be circumvented.

One of the more esoteric syringe designs is shown in U.S. Pat. No. 4,874,372 which uses a soluble composition to connect the plunger to the piston in a syringe, relying upon the aqueous medium of the medication to dissolve this mechanical link. Contamination of a medicant with such a soluble composition makes this syringe less than attractive.

Of course, it is not only drug addicts who attempt to re-use disposable syringes which have become contaminated. Economics often cause individuals with laudatory motives to neglect to guard against infections when utilizing disposable syringes multiple times.

The syringe of this invention overcomes some of the problems as discussed in the above prior art devices while maintaining a simple, economical syringe which more often than not defeats steps to circumvent its "one shot" use feature.

Another feature, not shown in the prior art devices noted above, as shown in the preferred embodiment of this invention, is the ability to retract the needle into the syringe barrel after use, further disabling the novel syringe, whereby the public at large will be prevented from accidental or inadvertent "pricks" of contaminated needles of disposable syringes. In the prior art, some syringes have a nested sleeve on the outside of the syringe body which can be extended to cover the needle after use. Further it is common to replace the needle cover employed for shipping after the syringe is used. However, medical personnel have actually "pricked" themselves with contaminated needles when replacing such covers.

The preferred embodiment of this invention allows the user to retract a contaminated needle into the body of the syringe without exposure to needle "pricks." Further this design includes a feature making it virtually impossible to be exposed to the needle once it is retracted into the syringe body. Prior art syringes having an outer sleeve to cover the needle after use are only partially effective as this cover can be easily broken away or mechanically forced back onto the syringe body, thereby exposing the contaminated needle once again.

SUMMARY OF THE INVENTION

In a syringe having a hollow cylindrical barrel with one closed end, a plunger having a length longer than the barrel mounted in the barrel for reciprocation, a handle on the distal end of the plunger extending from the barrel and a piston mounted on the opposite end of the plunger in the barrel along with a hypodermic needle mounted in the closed end of the barrel being in communication with the interior of the barrel, the improvement of including a hollow tapered section being formed in the barrel adjacent to its closed end, and a disabling means operable to disable the syringe as the disabling means associated with the plunger traverses this tapered section.

In one embodiment the piston end of the plunger includes a mechanical stop means operable to prevent withdrawal of the piston end of the plunger from the tapered section due to an engagement with the wall of the tapered section by the stop means which is too small in diameter to engage the wall of the barrel in its untapered section. In another embodiment said tapered section is operable to collapse the piston of the syringe as it transverses the tapered section whereby the piston thereafter will not seal with the tapered section or the barrel when withdrawn from the taper section.

A more desired embodiment is an improved syringe having a hollow cylindrical barrel, a plunger having a length longer than the barrel mounted in the barrel for reciprocation, a handle on the distal end of the plunger extending from the barrel and a piston mounted on the opposite end of the plunger in the barrel, a hollow sleeve with a closed end slidably mounted in the barrel, a hypodermic needle mounted in the closed end of this sleeve with communication into its interior, stop means associated with the piston end of the plunger operable to prevent withdrawal of the piston end of the plunger from the sleeve whereby withdrawing the plunger from the barrel after its piston end has entered the sleeve will pull the sleeve and its attached needle into the barrel encasing the needle and thereafter preventing persons from being "pricked" by the sharp end of the needle when the novel syringe is discarded.

BRIEF DESCRIPTION OF THE DRAWINGS

The invention of the applicant will be understood by reference to the accompanying drawings, in cooperation with the accompanying description, wherein:

FIG. 1 is a section of one of the most elementary embodiments the novel syringe constructed according to this invention;

FIG. 2 is a section of a piston and a plunger of a syringe being another elementary embodiment, with part of the plunger broken away, illustrating a collapsible piston used in this embodiment;

FIG. 3 is a section of a piston and a plunger, with parts broken away, illustrating a dowel and socket connection between the plunger and the piston for a syringe having a split washer disconnect feature which is yet another embodiment of the invention;

FIG. 4 is a perspective of the split washer used in the embodiment shown in FIG. 3;

FIG. 6 is a section of the novel syringe illustrated in FIG. 5;

FIG. 7 is a section, similar to the section shown in FIG. 6 wherein the hypodermic needle is illustrated in a retracted position after the syringe has been utilized;

FIG. 8 is a section of a further embodiment of the novel invention providing for retraction of the hypodermic needle into the syringe body after the syringe has been employed;

FIG. 9 is a section of the novel syringe shown in FIG. 8 showing the needle retracted into the syringe body and the piston collapsed by the taper in the syringe barrel.

DESCRIPTION OF A PREFERRED EMBODIMENT

Figure 5:
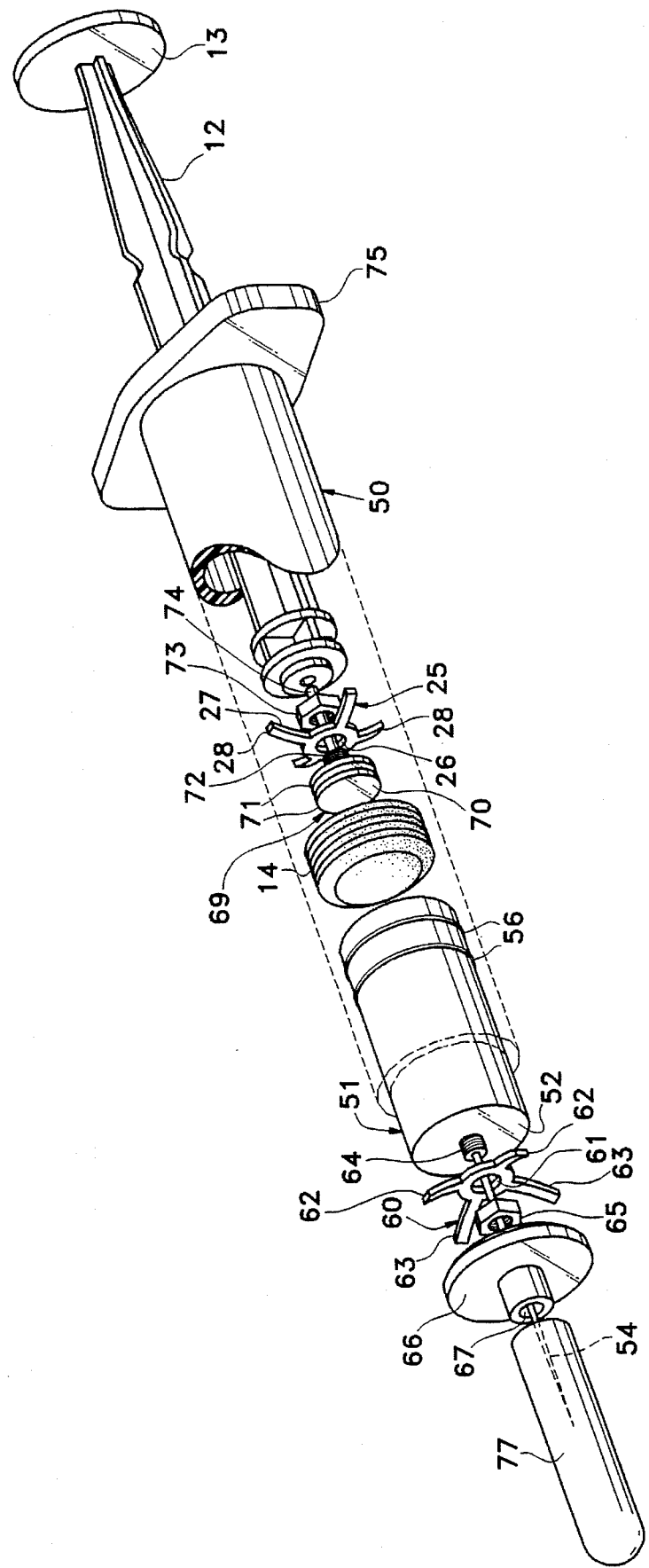
FIG. 5 is an exploded perspective of one of a more preferred embodiment of the invention with parts broken away having a needle retracting feature obtainable with this invention.

Referring to FIG. 1 it can be seen that the novel syringe 10 of this invention employs a cylindrical hollow barrel 11 which forms its principal component. Mounted in the barrel for reciprocation is a plunger 12 which has a length slightly longer than the barrel so one end stacks out the end of the barrel when it is inserted. At the distal end of the plunger extending from the barrel is a cap or handle 13 that provides a flat surface to apply pressure to force the plunger into the barrel for an injection stroke. At the end of the plunger inserted into the barrel is a piston 14 which is mounted on this end of the plunger.

Normally an end cap 15 is fitted to the end of the barrel 11 of the syringe 10 opposite the projecting end of the plunger 12 to close it; alternatively the end cap can be formed as part of the barrel as shown in FIG. 1. Centrally disposed in this end cap is a hollow hypodermic needle 16 which is in communication with the interior of the barrel so that a fluid medicant can be forced from the barrel and into the hollow core of the needle. This needle construction is typical of most syringes.

The novel syringe 10 of this invention, in the embodiment being described, differs from conventional syringes in that hollow barrel 11 includes a internal tapered portion or section 11a starting in its central portion and tapering to increasingly smaller diameters as the end cap is approached, as best shown in FIG. 1. It will be appreciated that as the piston 14 approaches the end cap 15 it will constricted to a smaller and smaller diameter. However as this occurs the seal between the piston and the wall of the tapered portion is not breached, but enhanced.

In the embodiment of the invention shown in FIG. 2, the piston 14a is constructed with a collapsible core structure 20 surrounded with a Neoprene® or other similar elastomer cover 21. The cover includes circular sealing lands 22 about its outer periphery. Since the cover is stretched over the core, as the piston traverses the ever decreasing diameters of the tapered section 11a, the core structure will be uniformly reduced in diameter with the Neoprene® or other elastomer cover shrinking to the new core size. Thus, once the piston traverse the first part of the tapered portion of the barrel 11 it will be too small in diameter to seal between the piston and the barrel if the plunger 12 is used to withdraw the piston. Solid plastic foams are suitable for forming the core structure 20.

The plastic foam of core structure 20 is formed on a pair of radial projecting lands 23 at the piston end of plunger 12 which has been modified to provide these lands. A larger radial projecting flange 24, inboard of these lands, provides a piston rest at the end of the plunger to stabilize the collapsible piston. As shown in FIG. 2 this piston rest is slightly larger in diameter than the core structure so it also engages the rim of the elastomer cover 21.

In these embodiments, since the syringe 10 is shipped with the plunger 12 extended (pulled half way out of the barrel, see FIG. 1) and, as the tapered portion 11a of the barrel 11 begins in the central portion of the barrel, the syringe can be filled with fluid medicant and air expelled by reciprocating the piston 14 or 14a in the cylindrical portion 11b of the barrel which is not tapered. The piston is designed to sealingly engage the barrel 11b even though the drawings, for the purpose of clarity, may illustrate a small clearance between the lands of the piston 14 and the bore of the barrel. As a result the medicant can be "pumped" into the syringe without bubbles or the like.

In a more preferred embodiment, shown in FIG. 1, a solid elastomer piston 14 is attached to the end of the plunger 12 inserted into the barrel. Also mounted on this end of the plunger is stop disk (means) 25, which is mounted between the plunger end and the piston (see e.g. FIG. 5). Typically the stop disk takes the form of a cupped, star-shaped circular disk having a central aperture 26, with a series of radially projecting arms 27 which are sharpened at their distal ends 28. At least three arms are required and it is mounted on the plunger so its cup faces away from the piston. The diameter of this disk is Just slightly less than the internal diameter of barrel 11 in the latter's un-tapered portion 11b. In view thereof the disk 25 will not impede the reciprocation of the piston in this part of the barrel. However, as the piston is forced into the tapered portion 11a of the barrel, the radially projecting arms 27 of the disk will immediately engage the circular wall of this section or portion of the barrel. Due to the cupped shape of the disk, inward travel of the plunger 12 and piston 14 during an injection stroke is not impeded; however if the direction of plunger 12 is thereafter reversed the sharp ends 28 of the projecting radial arms will then bite into the circular wall of the tapered portion and lock the piston in place.

If a dowel and socket joint 29 is used to connect the plunger 12 to a piston 14b (see FIG. 3), pulling hard on the plunger 12 with the stop disk installed will only cause the plunger to release the piston before plunger is finally extracted thereby rendering the syringe useless, as the stop means 25 will not release the piston.

The taper may also be used to disconnect the piston from the plunger 12 by using a slit washer 30 with a conical surface 31 which placed between a piston 14 and the plunger, as shown in FIG. 3. As the slit washer (see FIG. 4) is forced to a smaller diameter when traversing the tapered portion 11a of the barrel 11, the joint 29 between the piston and the plunger is forced apart. Since the piston is effectively wedged in the tapered portion by the injection stroke and is also disconnected from the plunger by the action of the split washer, it is impossible to reciprocated the piston thereafter.

To accomplish this disconnect feature the joint 29 is constructed with a dowel 32 extending from a conical surface 33 formed at the piston end of the plunger 12. This dowel includes a cap 34 on its distal end as shown in FIG. 3 which is received in socket 35 formed in a boss 36 on which piston 14 is mounted. As indicated, as the slit washer is decreased in diameter, when traversing the tapered portion of the barrel 11, it will dislodge the cap from the socket as the cap's purchase therein is designed to be minimal.

The most preferred embodiment is shown in FIGS. 5, 6 and 7. In this embodiment a different hollow cylindrically barrel 50 is used which is essentially a open ended tube, as shown in these figures. In one end of the barrel a hollow sleeve 51 is inserted. The sleeve has a closed end 52, which end has a central threaded nipple 64 projecting therefrom, as show in FIG. 7. A hypodermic needle 54 is mounted in this nipple so its hollow core communicates with the hollow interior of the sleeve. The sleeve fits snugly in the barrel but is sized to slide inside the barrel.

As can be seen in FIG. 6 from the open end or mouth 55 of the sleeve 51 its hollow interior is tapered so as it progressed toward its closed end 52 it has over decreasing diameters. This is functional equivalent of the tapered portion 11a of the barrel 11 described above. However there is a major distinction in that the sleeve is not formed as part of the barrel 50 and is slidable therein with a fluid seal so no medicant can escape between the bore of the barrel and the sleeve.

The circular exterior of the sleeve 51 may include a plurality of sealing lands 56 which ensure a sealing relationship with the internal wall or bore of the barrel is always maintained. Alternatively a small o-ring (not shown) can be used in place of the lands on the outer surface of the sleeve. Further the rim of the mouth of the sleeve is feathered so there is a smooth transition for the piston 14 from the barrel to the interior of the sleeve.

Once the sleeve 51 is inserted into one end of the barrel 50 with the needle 54 projecting therefrom, a cupped, star-shaped circular disk 60 (stop means) having a central aperture 61, with a series of radially projecting arms 62, which are sharpened at their distal ends 63, is inserted over the nipple 53 so it is cupped away from the sleeve. This disk is then secured on the threaded nipple 53 by a nut 65 or the like. The arms of disk circumscribe a diameter slightly larger than the inside diameter of the barrel 50, and, as a result the disk will allow the sleeve 51 to move into the barrel but prevent any movement in the opposite direction. An end cap 66 with a central opening 67 is attached to the end of the barrel, as shown in FIG. 5, and 6 so the needle 54 extends through this opening. This opening may be slightly off set (not shown in the drawings) so the needle is deflected slightly as it passes through the opening in the end cap. As a result once the needle is withdrawn into the barrel it will no longer line up with the opening in the end cap. If this feature is used the stop means may be eliminated.

In this embodiment, as in the previously described embodiment, shown in FIG. 1, a solid elastomer piston 14 is attached to the end of the plunger 12 inserted into the barrel 50. Also mounted on this end of the plunger is stop means 25, which is mounted between the plunger end and the piston. As previously described the stop means takes the form of a cupped, star-shaped circular disk 25 having a central aperture 26, with a series of radially projecting arms 27 which are sharpened at their distal ends 28. At least three arms are required and it is mounted on the plunger so its cup faces away from the piston. The diameter of this disk is just slightly less than the internal diameter of barrel 50. In view thereof this disk will not impede the reciprocation of the piston in this part of the barrel. However, as the piston is forced into the hollow sleeve 51 the radially projecting arms of the disk will engage the circular wall of sleeve. Due to the cupped shape of the disk, the inward travel of the plunger 12 during an injection stroke is not impeded; however when the direction of plunger is thereafter reversed, the sharp ends projecting radial arms will bite into the circular wall of the sleeve and lock the plunger to the sleeve when ever this reversal of direction occurs. When the plunger is thereafter extracted, it will pull the sleeve and its associated hypodermic needle further into the barrel 50, and eventually completely enclose the needle, as shown in FIG. 7. If desired the plunger 12 may include a weakened section 68 so it can be broken off once the needle has been retracted into the barrel of the syringe.

In the exploded view of this preferred embodiment is shown in FIG. 5, it can be seen a plug unit 69 is used to attach the stop means 25 to the piston end of the plunger 12. This plug unit includes a boss 70 which has lands 71 to attach the piston 14 to the boss. This boss also has a projecting threaded nipple 72 on which the disk 25 is mounted and secured with a nut 73. A shaft 74 extending from the nipple is received in the end of the plunger 12 to attach this piston assembly to the plunger.

Also, typically of all the syringes described, a finger-rest 75 is provided at the plunger end of the barrel which has a central aperture 76 for plunger 12, as shown in the several drawings. Also such syringes usually employ a needle guard (cover) 77 which is attached to the end cap of the syringe 10 to cover its associated hypodermic needle. This guard keeps the needle sterile and prevents inadvertent pricks by the exposed end of the sterile needle.

One of the advantages of this invention is that is it economical to construct because it requires no complicated molds to manufacture. While in the preferred embodiment a number of parts are illustrated the construction can obviously be simplified for production purposes.

Variations on the design described herein are possible without departing from the spirit of the invention. For example the length of the tapered section can be varied and the length of the sleeve changed without departing from the design.

Figure 10:
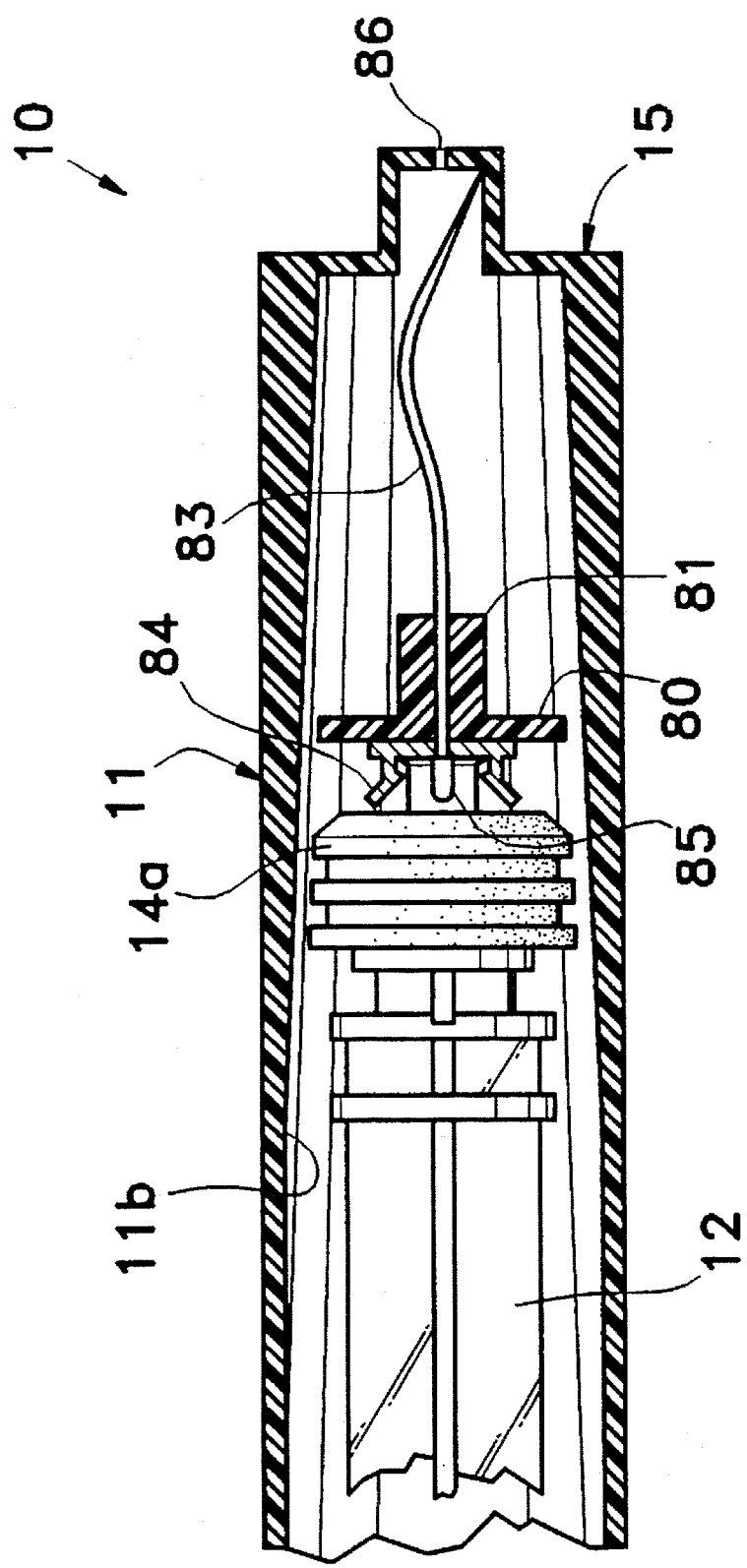
FIG. 10 is a partial section of the syringe illustrated in FIG. 9 showing that the needle is "jammed" inside the syringe body when the plunger is depressed after the needle has been retracted into the syringe body or barrel.

In FIGS. 8, 9 and 10 a different combination of some of the inventive features is illustrated. While the device is essentially similar to the novel device shown in FIG. 1, the needle end of the barrel 11 is modified, as is the end of the piston 14a.

At the needle end of the barrel 11 a flat disk 80 is inserted having an extending boss 81 which is received in a central bore 82 formed in the closed end 52 of the barrel. The hypodermic needle 83 is mounted in the boss so its hollow core will be in fluid communication with the inside of the syringe body when the disk (assembly) is inserted therein, as shown in FIG. 8. On the top of this disk are four barbs 84 which form one half of a connecting unit. The other half of the connecting unit is a flanged cap 85 fixed to the central end of plunger 14a.

When the injection stroke is completed the flanged cap 85 is engaged by the barbs 84 and these parts lock together. Thus, when the plunger 12 is withdrawn it will pull the disk 80, and its attached needle 83, into the syringe barrel 11, as shown in FIG. 9. This connecting unit is much like the terminal connections on a 9-volt battery. However, any number of different connecting means can be used to connect the plunger to the hypodermic needle assembly. It is anticipated a simpler connection will be used commercially.

In the embodiment shown in FIGS. 8, 9 and 10, the hypodermic needle 83 is slightly curved and passes through a small opening 86 in the needle end of the barrel 11 as shown in FIG. 9. Thus when the needle is withdrawn into the syringe body the needle's point will no longer align with this small opening. As a result, if the plunger is pushed into the barrel after the needle is retracted, the needle will engage the inside end of the barrel and bend or break, as shown in FIG. 10.

The principles are aptly illustrated by the design illustrated in FIG. 8, 9 and 10. However, it will be appreciated the connection between the piston and needle assembly may be recessed or changed to avoid the loss of an medicant effected by the spacing illustrated in these drawings. For example, the disk 80 and boss 81 can be replaced by a clasp (not shown) attached on the end of the needle 83 and the boss 81 replaced by an elastomer plug in bore 83 (not shown) whereby the clamp will engage the cap 85 and the needle will be extracted through the elastomer plug as the plunger is withdrawn. Obviously the needle will not re-align with bore in the plug, even if the needle is not curved, and therefore will be bent or broken as shown in FIG. 10 as its point embeds in the elastomer plug when the plunger is thereafter pushed into the syringe body or barred 11.

Other embodiments are possible without departing from the general concepts described herein.

Having described my invention, I claim:

1. In a disposable syringe having a hollow cylindrical barrel closed at one end, a plunger mounted in said barrel for reciprocation, said plunger having a handle on its end extending from the barrel and a piston mounted on the opposite end of said plunger received in said barrel and a hypodermic needle mounted in said closed end of said barrel being in communication with the interior of said barrel, the improvement comprising:

first means formed in said barrel adjacent to its closed end operable to disable said syringe as said piston approaches the needle end of said syringe; and second means associated with the piston end of said plunger and said hypodermic needle operable to couple said plunger and needle when said piston engages said needle end of said barrel and to retract said hypodermic needle into said barrel of said syringe when said piston end of said plunger is moved away from the needle end after said second means has coupled said piston end of said plunger with said hypodermic needle whereby said hypodermic needle can be safely retracted into said barrel of said syringe after it has been used.

2. The improved syringe defined in claim 1 wherein stop means are included in the barrel of the syringe operable to prevent the hypodermic needle from emerging from said barrel after it is retracted into said barrel.

* * * * *